United States Patent [19]
Goldberg et al.

[11] Patent Number: 4,717,341

[45] Date of Patent: Jan. 5, 1988

[54] ORTHODONTIC APPLIANCE SYSTEM

[76] Inventors: A. Jon Goldberg, 74 Rumford St., West Hartford, Conn. 06107; Charles J. Burstone, 252 Old Mountain Rd., Farmington, Conn. 06032

[21] Appl. No.: 817,925

[22] Filed: Jan. 13, 1986

[51] Int. Cl.[4] .................................................. A61C 3/00
[52] U.S. Cl. .................................... 433/9; 433/222.1; 433/22; 428/238; 428/373
[58] Field of Search ...................... 433/22, 9; 428/238, 428/373, 902

[56] References Cited

U.S. PATENT DOCUMENTS

| 4,386,908 | 6/1983 | Keery | 433/9 |
|---|---|---|---|
| 4,433,960 | 2/1984 | Garito et al. | 433/9 X |

FOREIGN PATENT DOCUMENTS

| 2553655 | 4/1985 | France | 433/9 |
|---|---|---|---|
| 2129307 | 5/1984 | United Kingdom | 433/9 |

*Primary Examiner*—Nancy A. Swisher
*Attorney, Agent, or Firm*—Chilton, Alix & Van Kirk

[57] ABSTRACT

A force imparting orthodontic appliance system is provided wherein the components thereof are formed from fiber reinforced composite material comprising a polymeric matrix and at least five percent of a reinforcing fiber embedded in the matrix.

15 Claims, 3 Drawing Figures

ORTHODONTIC APPLIANCE SYSTEM

BACKGROUND AND SUMMARY OF THE INVENTION

The present invention relates generally to appliances used in dentistry and is more particularly concerned with a new and improved appliance system used principally in orthodontics but also having application to prosthetics and oral surgery.

As is well known, orthodontic appliances are used to move or manipulate certain teeth to correct irregularities and/or abnormalities in their relationships with surrounding members. This is achieved by the application of systems of force that have their origin primarily in elastically-deformed wires which absorb and release energy during loading and unloading. Heretofore, the force-imparting wires used in orthodontic treatment have been made from certain metal alloys, such as 18-8 stainless steel, chrome-cobalt-nickel (CCN) alloys, such as those sold under the tradename "Elgiloy" and, more recently, from titanium containing alloys that take advantage of the bending and torsional properties of those materials. With the earlier materials efforts were directed almost exclusively toward the development of optimum appliance configurations with only ancillary consideration being given to the material used for the appliances.

Proper application of the correct forces requires not only the study of suitably contoured and clinically dimensioned shapes or configurations together with variations in the cross-sectional dimensions of the force-imparting wire, but also a better understanding of the biomechanism involved in orthodontic appliances.

Desirable tooth movement can best be achieved by producing an optimal force system capable of delivering relatively light but continuous corrective forces. The primary or basic biomechanical characteristics include a moderate to low force magnitude whereby the teeth will move rapidly and relatively painlessly with minimum tissue damage, a constant force level over time as the appliance experiences deactivation in order to provide maximum tissue response, an accurate location of the point of application of the force or its equivalent and a uniformity in the force applied through the total distance over which the force acts. It also is desirable to provide within an orthodontic appliance the ability to undergo large deflections without deformation. Of course, if the force acting on the teeth decays too rapidly, the teeth will move more slowly and it becomes more difficult to accurately produce the desired effect.

Heretofore, the force magnitude applied to the teeth is produced in part by the cross section of the wire used in the appliance, with smaller wires providing the desired lower or reduced force. Primarily, however, the smaller wires are used to achieve large deflections. As will be appreciated, larger wires fit well in the slots of band-mounted or direct bonded brackets and a good fit is necessary for controlled tooth movement. If the wire and the bracket are not properly matched, the play between those members leads to loss of control. Reduction in slot or lumen size may be undesirable since (1) it may be more difficult to control tolerances and (2) manufacturing variations in alloy wire cross section have a proportionately greater effect on force magnitudes. Despite this, a reduction in the wire cross section with its attendant reduction in load-deflection rate and increased range historically has been the course followed to achieve force constancy using 18-8 stainless steel wire. In this connection, care must be taken since too great a reduction in cross section can result in permanent deformation before optimal forces are reached.

Although the principal and predominant emphasis in orthodontic research has been on improved appliance design, and relatively little attention has been given to alternatives for the conventionally employed 18-8 stainless steel or the chrome-cobalt-nickel alloy wires, efforts are now being made in providing the aforementioned desirable biomechanical characteristics through the use of alternative titanium alloy materials. One example of such an approach can be found in the proposed utilization of Nitinol alloys of the type described in U.S. Pat. No. 3,351,463. These materials are near-stoichiometric intermetallic compounds of nickel and titanium, preferably having cobalt substituted for the nickel on an atom to atom basis. The alloy can be preformed below its critical transition temperature and, when heated to above that temperature, will display a mechanical memory causing the material to return to its predisposed shape. The application of this material to orthodontics is set forth in U.S. Pat. No. 4,037,324 where the longitudinal shrinkage characteristic of the wire is used. Although this intermetallic material is reported to be quite ductile, it has been found in practice that the material will not withstand cold bending into major orthodontic configurations and cannot be used for closing loops and the like. This, of course, severely limits the alloy's use in the formation of appliances that require significant bends in their design. Additionally, the material cannot be welded or soldered, thereby substantially hampering its utilization. In fact, the only way to join this wire, Nitinol, is by mechanical means. Furthermore, metal wires such as these are not aesthetically pleasing and it is difficult to product specialized shapes and cross sections from this material.

Our prior development using beta titanium alloys as reported in U.S. Pat. No. 4,197,643 solved many of the problems encountered when using stainless steel or Nitinol while, at the same time, facilitating the delivery of optimum orthodontic forces. That material can be easily joined, exhibits a low stiffness or modulus of elasticity while providing a preferred low force magnitude and force constancy over a prolonged period of time to achieve continuous, relatively painless tooth movement with maximum tissue response and minimum tissue damage. However, the material lacks optimum formability for providing customized shapes for a particular situation and is not aesthetically pleasing.

Although orthodontists are now beginning to control force systems through the use of material selection as well as by appliance design, the properties of the available materials limits their use. In this connection, there are several aspects or clinical parameters which are important for all orthodontic appliances and relate to both the wire and the attachments which include the brackets and tubes. For the wires these include springback, stiffness, formability, joinability and aesthetics as well as shape and dimension. The characteristics of the attachments involve considerations such as geometry, bonding to the teeth, attachment of wires, aesthetics and ease of manufacture.

The elastic deformation or springback parameter is a measure of the amount of deflection or activation which the appliance can sustain and still be totally elastic, that is, recover to its original shape and position. This feature is important because it determines the distance over which an appliance can effectively act before readjustment by the orthodontist is necessary. Appliances which can sustain larger deflection can more readily engage teeth which are more severly malopposed. The elastic deflection or springback of an appliance is fundamentally proportional to its ratio of flexure strength to flexure modulus or similarly its ratio of tensile yield strength to modulus of elasticity.

The stiffness of an appliance is important because it is a primary determinant of the force which will be applied to the teeth. Greater stiffness results in more force for each unit of activation. Appliance stiffness is proportional to the material's flexure modulus and for isotropic materials, its tensile modulus. Thus materials of lower modulus of elasticity have a lower stiffness.

In most clinical situations, wire or appliances have to exhibit sufficient formability to be formed to a desired customized shape for a particular case. Additionally, they have to be joined while retaining their strength and elasticity characteristics, and they must be of the desired cross-sectional shape and dimension.

Of course, aesthetics also is an important consideration, particularly for all labial appliances. All metal wires and brackets are gray or silver in color and are quite obvious against the white background of the tooth structure. Consequently, the use of clear or tooth-colored appliances would be considerably more aesthetically pleasing to many patients.

The brackets, tubes, ligature wires and related attachment components that translate the force from the wire directly to the tooth also have various characteristics which have to be considered for any orthodontic appliance. For example, the design, geometry and overall dimensions of the attachment are important for both its ease of manipulation as well as its ability to help contribute to the active aspects of the orthodontic force system. Attachments are often bonded directly to the tooth surface without the use of a band which circumscribes the entire tooth. An attachment which is bonded directly requires certain functional shapes and contours on the surface which will contact the tooth in order to obtain satisfactory bonding. Further the attachments should be easy to fabricate or manufacture.

Unfortunately, the alloys that have a high elastic deflection, such as the nickel titanium alloys, cannot be readily formed and can be joined only by mechanical means. On the other hand, stainless steel which probably has the lowest elastic deflection, is very formable and can be joined by soldering, albeit this is an operator sensitive procedure.

It is also important to note that nuclear magnetic resonance diagnostic testing is becoming more popular and there are some predictions that in the future it may replace the CAT scan in certain diagnostic procedures. Metallic orthodontic appliances of the type that have been used heretofore have specifically been identified as a problem area for this diagnostic procedure since the metal does not exhibit the requisite radiolucency and interferes with the resulting images.

Attempts have been made to fabricate some brackets from polycarbonate and ceramic materials in an attempt to obtain a more aesthetic appliance. However, the polycarbonate brackets cannot resist the high stress magnitudes frequently encountered in orthodontics and typically fail at torque levels well below the levels obtainable with conventional stainless steel arch wires. The ceramics are expensive, not available in the more complex shapes and sizes and are brittle.

Accordingly, it is an object of the present invention to provide a new and improved orthodontic appliance system that facilitates the application of a given force with greater ease and accuracy while customizing both the stiffness and strength characteristics of the appliance thereby providing an associated increase in the effective working time of the appliance while meeting the necessary criteria of biocompatibility, formability, environmental stability, aesthetics and ease of joining and bonding.

Another object of the present invention is to provide a dental appliance system of the type described that provides improved springback coupled with the ability to change or vary the stiffness of the wires without changing their size and allow for the fabrication of unique wire/bracket engagement designs using facile manufacturing techniques.

Still another object of the present invention is to provide an orthodontic appliance system of the type described that utilizes a new and improved force-imparting material capable of exhibiting a lower modulus of elasticity than prior alloys, high elastic deflection and a selective ratio of yield strength to modulus of elasticity while reducing the need for periodic installation of wires of varying cross section. Included in this object is the provision for the use of a material permitting more compatible cross section, shape and dimension in both the wires and the attachments while minimizing the need for closer wire tolerances. Also included is the provision for wires whose force magnitudes and moment to force ratios are controlled by selection of the modulus of elasticity rather than the traditional approach of simply modifying the cross section thereby providing an expanded sequence of wires that would make "constant cross section orthodontics" clinically feasible.

Still another object of the present invention is to provide a new and improved dental appliance system of the type described that utilizes materials covering a broader spectrum of desired characteristics and is capable of being formed into a wide array of orthodontic appliances from the simple to the highly complex orthodontic configurations in order to deliver the optimum moment to force ratios, improved control through early and accurate bracket engagement, ease of handling, accurate centers of rotation of the tooth as it is moved and simplified attachments and instrumentation. Included in this object is the provision for the use of a composite material capable of taking advantage of the qualities of its separate components coupled with significantly enhanced aesthetic characteristics.

A further object of the present invention is to provide a new and improved dental appliance system of the type described which utlizes fiber reinforced composite materials of excellent formability, joinability and appearance while simplifying manufacturing operations. These materials can be used not only for simple wires but also for many components of intraoral fixed appliances which include arches, segments, hooks, tiebacks, ligature wires and springs, pins, brackets, tubes, active lingual appliances and other mechanisms. They may also be used for removable and extraoral appliances such as headgears.

A still further object is to provide a system of the type described that employs fiber reinforced composite material and includes the ability to deliver lower forces for a given deflection and more constant force levels with time due to a lower load-deflection rate, to change wire stiffness over a continuous range without changing the cross-sectional dimensions of the wire, to allow engagement of more severe dental malrelations and increase the "working time" or "working range" of the appliance and to increase the ease and accuracy of applying a given force. Included in this object is the provision for system designs that can be coordinated with the material properties to optimize each and facilitate the use of unique and more convenient shapes.

Other objects will be in part obvious and in part pointed out more in detail hereinafter.

These and related objects are achieved in accordance with the present invention by providing an orthodontic appliance fabricated from a fiber reinforced composite material with the force delivery component having a flexure modulus of elasticity between $0.3 \times 10^6$ and $30 \times 10^6$ psi and a ratio of yield strength to modulus of elasticity up to at least about $40 \times 10^{-3}$. The composite consists essentially of a polymeric matrix and a fiber component embedded within the matrix with the fiber component constituting greater than 5 percent by weight of the composite material. The system is particularly efficacious in providing materials having moduli of elasticity beyond the scope of those provided by the metal alloys utilized heretofore coupled with desirable strength characteristics and improved aesthetic qualities.

A better understanding of the invention will be obtained from the following detailed description and the accompanying drawing as well as from the illustrative applications of the invention including the several components of the invention and the relation of one or more of such components with respect to each of the others as well as to the features, characteristics, compositions, properties and relation of elements described and exemplified herein.

DESCRIPTION OF THE PREFERRED EMBODIMENT

Although control and prediction of force systems has been a focus of orthodontic treatment, traditionally this has been achieved through variation in wire size, and appliance design. Whether it is being used orthodontically or in other applications, the bending stiffness of a cantilever is equal to the product of its modulus of elasticity and its moment of inertia. Since the modulus of the commonly used stainless steel and CCN alloys are about the same, the modulus was usually treated as a constant and the appliance stiffness and range of deflection were controlled by wire size, span length and design. As metioned hereinbefore, within the past few years beta titanium, nickel-titanium and multistranded or braided wires have been introduced to the orthodontic profession. These alternative alloys have received general acceptance and their popularity continues to increase. The new alloys, like beta titanium, allow for improved and/or simplified designs because their modulus and ratio of yield strength to modulus are significantly different from the earlier commonly used alloys.

In accordance with the present invention it has been found that force systems can be controlled during treatment by using wires made from fiber reinforced composite materials with different moduli of elasticity, allowing the cross-sectional dimensions to be kept constant. This approach advantageously provides improved control through early and accurate bracket engagement, ease of handling and simplified attachments and instrumentation. This system enables the use of an expanded sequence of wires and attachments which are customized or designed for integrated use and make constant cross section orthodontics clinically feasible.

Figure 1:
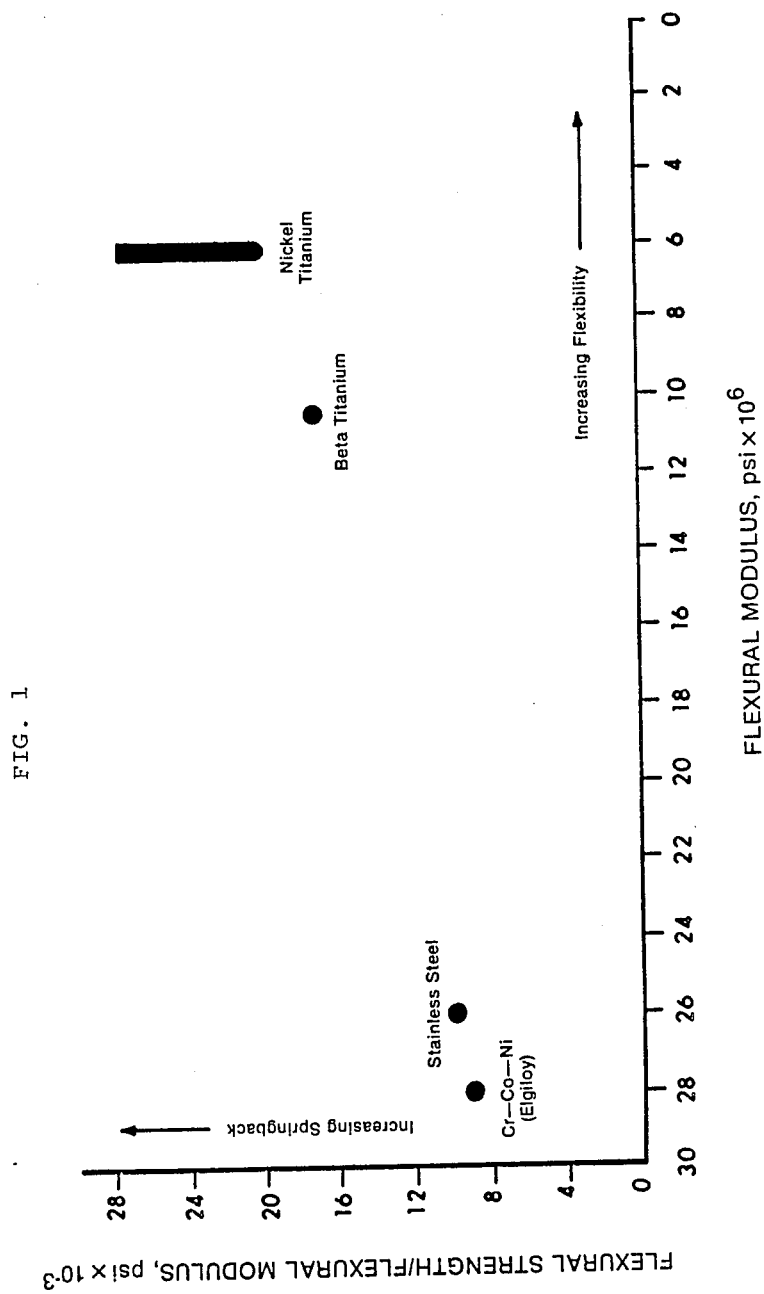
FIG. 1 is a graph depicting the relationship between the stiffness and springback characteristics of the metal alloys used heretofor for various orthodontic devices.

Referring now to the drawing in greater detail and particularly to the graph designated as FIG. 1, the springback or maximum elastic bending deflection is plotted against the stiffness or modulus of elasticity for commercially available orthodontic materials. As can be seen, the stainless steel and CCN materials exhibit the highest modulus values, approximately $27 \times 10^6$ psi, and the lowest springback. The lowest modulus is found in braided or multistranded wires, with values of $1-2 \times 10^6$ psi while the beta titanium and nickel-titanium alloys are located at approximately 10 and $6 \times 10^6$ psi, respectively. It is readily apparent that a large gap exists in the $12-24 \times 10^6$ psi modulus region which, if filled, would provide more versatility in the selection of wires and a more uniform progression in the stiffness or flexibility characteristics of orthodontic devices. It is also known that the materials exhibiting the desirable low stiffness characteristics tend to lack adequate strength while any increase in stiffness is necessarily accompanied by a decrease in elastic deflection or springback.

Figure 2:
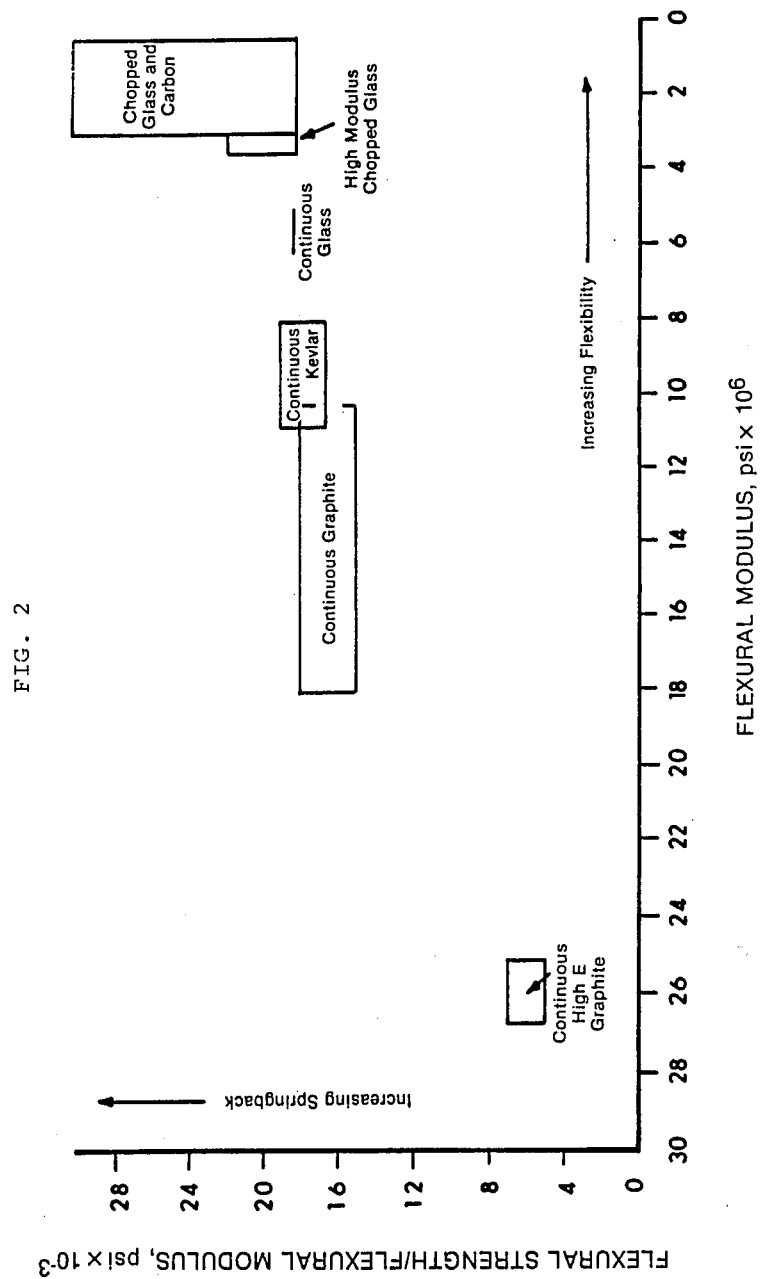
FIG. 2 is a graph similar to FIG. 1 depicting the same characteristics for the fiber reinforced composite materials of the present invention.

FIG. 2 uses the same axes and exemplifies the properties obtained with the fiber-reinforced composites of the present invention. As shown, the flexural modulus and strength can be varied continuously and over a wide range by adjusting the composite utilized to provide the desired characteristics. As shown, these materials exhibit flexure modulus values ranging from about $0.5 \times 10^6$ to $25 \times 10^6$ psi, and elastic deflection ratios from about $4 \times 10^{-3}$ to about $30 \times 10^{-3}$.

The composite material utilized in the present invention is composed of two major components; a polymeric matrix and fibers embedded in the matrix. The fibers may take the form of long, continuous filaments or may be short fibers of uniform or random length. Where the composites take the form of elongated wires, the fibers are at least partially aligned and oriented along the longitudinal dimension of the wire. However, depending on the end use, the fibers may be otherwise oriented even to the point of being normal or perpendicular to that dimension to provide specific characteristics such as maximum torsional strength. When used for other orthodontic attachments, the short fibers may have a more random orientation throughout the matrix. It is a feature of the present invention that the composite material may be used to produce devices having unusual anisotropic properties. These propoerties can be tailored through the use of various fabricating techniques including the orientation of the fibers within the composite material as well as the percent of fiber used. This feature is particularly important since orthodontic force systems are three dimensional and control of the system in all dimensions is critical. Wires are made rigid in a buccallinqual or occlusal-gingival direction and of low stiffness in a torsional direction or the wires are specifically designed for torsional effects. For example, to allow tipping of incisors during retraction with full control over arch width and tooth alignment a different rigidity is used. This effect can not be produced by metal wires, whose properties are isotropic.

Although a variety of fibers may be employed, the most commonly utilized fibers are glass, carbon and/or graphite and polyaramid fibers, such as the fibers sold under the tradename "Kevlar." Other materials such as polyester, polyamides, and other natural and synthetic materials compatible with the particular matrix may also be employed to provide selective properties.

As mentioned, these fibers may take the form of short fibers or of continuous filaments such as continuous glass or graphite filaments. Typically, the short fibers will vary in fiber diameter or denier as well as in fiber length and it is preferred to utilize a range of fiber lengths and diameters with the shorter fiber lengths generally being preferred for certain applications. By shorter fiber length, we mean fibers having a length of about ⅛ inch or less although good results can also be obtained using fibers up to an inch in length where chopped or discontinuous fibers are employed. As will be appreciated, filament lengths can also vary, although these are more typically referred to as continuous length material as distinguished from the short fibers. The fiber diameter may vary from about 1.5 to 15 denier for synthetic materials. The inorganic materials such as glass and carbon fibers are usually finer with glass fibers falling in the low micron and sub-micron diameter range. A typical range for glass fibers is about 0.3-9 microns. For certain applications, it is also possible to use woven and nonwoven fibrous materials particularly where certain requisite strength characteristics are dictated by the specific structure being fabricated.

Figure 3:
FIG. 3 is a photomicrograph of a section of a fiber reinforced composite wire of the present invention.

In accordance with the present invention, it is preferred that a predominant number of the fibers are aligned along the longitudinal dimensions of the wire. This orientation is very desirable and is best seen in the photomicrograph of FIG. 3. In that view the well dispersed array of short glass fibers can be readily seen, as can the predominant alignment of the fibers. In this sample the glass fibers were dispersed within a nylon matrix at a fiber level of about 43 percent by weight. Similar orientation characteristics are attaned at lower fiber concentrations, e.g. at fiber levels of 10-25 percent. The orientation results in some degree from the production techniques used to form the resultant product but also is specifically designed into the devices. These techniques include molding operations, such as injection molding, that facilitate not only the production of unusual cross sections in the resultant product but also variations in cross section along the length of the force importing wires.

The short fibers not only enhance the variable production methods employed but also provide highly tailored properties including the plastic deformation or ductility of the end product. Where the end product includes attachments such as brackets, control over the orientation of the fibers in the matrix can key the effective retention of the wire at the desired angle to impart the necessary corrective force.

Where continuous fibers are employed, they are usually disposed in a parallel array relative to each other and are aligned along one dimension such as the major dimension of the device being produced. The continuous filament composite material is capable of providing a wire having modulus of elasticity beyond the range available with metal wires. For example, as contrasted with the low stiffness short fiber material that exhibits a modulus as low as $0.5 \times 10^6$ psi, the continuous filament material can be formulated to exhibit a modulus in the range of $1.5$–$30 \times 10^6$ psi and greater. As can be seen from FIG. 1 metals are not available for providing modulus levels in a significant portion of this range.

In addition to the greater range of stiffness values, the continuous filament material exhibits a larger or higher springback or percent elastic recovery. This permits the filament reinforced material to actively impart its force delivery capability with greater accuracy. Thus it can be seen that appropriate tailoring of the composite can be highly effective, particularly in regions where metals are not now available.

The polymeric materials employed as the matrix for the reinforcing fibers may be either thermoplastic or thermosetting materials and may involve a wide variety of polymeric materials. For example, the polymeric material may include polyamids such a nylon 6—6, polyesters, polyethylene terephthalate glycol, polycarbonates, polyolefins such as polypropylene or polyethylene, polyarylates, polyurethanes, ABS, polysulfones, polyacetals, polyphenylenesulfides or a wide variety of other polymeric compositions including vinyl esters and epoxy-type materials.

The characteristics of the materials may also be altered or enhanced through the use of various additives. For example the lubricity of the polymeric material may be enhanced by the use of fluoro compounds such as Teflon or similar fillers.

As indicated, the final properties of the fiber reinforced composites may vary not only with the individual materials utilized in the composition but also with the volume ratio of fiber to polymer matrix as well as the diameter or denier of the particular filaments being employed. Thus, as can be appreciated, the volume percent of fiber in each composition may vary within a wide range extending from as little as about 5 percent up to about 75–80 percent of the total composition of the composite material. As can be expected, the stiffness or flexure modulus of the material will increase with increasing amounts of fiber as will the yield strength of the material. However, it is an important feature of the present invention that the composite material also can be intentionally designed to be anisotropic in contrast to the nearly isotropic properties of the metal alloys used heretofore for orthodontic purposes. This is possible because of the heterogeneous nature of the fiber reinforced composites as well as by the fiber orientation and the percent of fibers used within the composition. Thus, it is possible in accordance with the present invention to provide significantly different properties in torsion and in flexure so that an appliance can be made to be very stiff in flexure but very flexible in torsion. This feature is particularly important since orthodontic force systems are three-dimensional and control of the system in all three directions is extremely important if not critical.

The following examples are given in order that the effectiveness of the present invention may be more fully understood. These examples are set forth for the purpose of illustration only and are not intended in any way to limit the practice of the invention. Unless otherwise specified, all parts are given by weight.

EXAMPLE 1

A fiber reinforced composition material was prepared from nylon 6—6 and 30 percent by weight of chopped glass fibers having a diameter range of about 8 to 12 micrometers and an average length falling within the range of 0.008 to ⅛ inch. The material was formed into an orthodontic wire having a generally rectangular cross section with dimensions of 0.019×0.025 inch. This wire was formed in a heated mold with the size selection for the wire being comparable to the conventional size used for orthodontic wires and at the same time of a size that will readily allow injection molding. The resultant wire had a flexure modulus of elasticity of $1.3 \times 10^6$ psi, a flexure strength of $38.0 \times 10^3$ psi and an elastic deformation ratio of $29.2 \times 10^{-3}$.

The resultant wire exhibited springback characteristics about 1.5 times greater than that currently available with multistrand stainless steel wires. The stiffness or modulus of elasticity of the material provided biologically desirable low forces while at the same time exhibiting improved aesthetics since the composition is able to be modified to provide a natural tooth coloration. The formability of the material was excellent and the rectangular design of the wire allowed for torque production and three-dimensional control. The low modulus and high ratio characteristics of this material make it well suited for initial orthodontic alignment functions since it facilitates significant tooth movement.

EXAMPLE 2

The same polymeric and fiber materials as used in Example 1 were utilized again to produce an orthodontic wire except that 60 percent by weight of the fiber was used in the composition. The resultant wire exhibited a flexure modulus of elasticity of $2.8 \times 10^6$ psi and a flexure strength of $50 \times 10^3$ psi resulting in a elastic deformation ratio of $17.8 \times 10^{-3}$. Such a formulation provides a low stiffness wire for initial or secondary alignment where greater tooth movement is required. At the same time it provides the biologically desirable low stiffness characteristics.

EXAMPLE 3

The procedure of Example 1 was repeated except that a polyester resin was used in place of the nylon. The particular polymeric material was polybutylene terephthalate sold by LNP Corporation under the tradename "WF-1006". The resultant wire had a flexure modulus of $1.2 \times 10^6$ psi, a flexure strength of $28 \times 10^3$ psi and a deflection ratio of $23.3 \times 10^{-3}$.

EXAMPLE 4

A fiber reinforced composite material was formulated from an amine-cured epoxy resin and 62 percent by volume of continous graphite strands having a diameter of $3.15 \times 10^{-3}$ inch. This material is a commercially available from Hercules Chemical Company under the tradename "Magnamite." When drawn into a continous orthodontic strand or wire, it exhibited a modulus of elasticity of $18.5 \times 10^6$ psi and an elastic deflection ratio of 14.1.

As can be appreciated, the characteristic of this material places it between the conventional stainless steel wire and the beta titanium material thereby providing stiffness characteristics not commonly available in orthodontic wires yet exhibiting an intermediate springback characteristic between these two conventional orthodontic materials. Such material is particularly well suited for wires and prefabricated springs for lingual and facial orthodontic assemblies requiring intermediate springback characteristics or where higher stiffness is required in a retaining wire. Additionally, it may be used as lingual arches and for labial applications where aesthetic considerations are not a factor. This is true since the graphite filaments in the high percentages used gives a greyish tone to the fabricated orthodontic wire.

EXAMPLE 5

A fiber reinforced composite material was prepared using 40 percent by weight of glass fibers within a polycarbonate matrix. The glass fibers were of the same size as in Example 1. The material was formulated into an orthodontic bracket that could be modified to produce a tooth coloration and could be injected molded into the required configuration. The material exhibited a flexure modulus of elasticity of $1.5 \times 10^6$ psi, a flexure strength of $30 \times 10^3$ psi and a Rockwell hardness of R118, M97.

EXAMPLE 6

The procedure of Example 5 was repeated using nylon 6—6 in place of the polycarbonate and increasing the amount of glass to 50 weight percent. The resultant orthodontic bracket exhibited a flexure modulus of elasticity of $2.2 \times 10^6$, a flexure strength of $46.5 \times 10^3$ psi and a Rockwell hardness of R121, M100. The mesialdistal width of the bracket was 3.0 mm. The slot was 0.41 mm (0.016 inch) wide and the wall thickness was varied from 1.0 to 2.5 mm.

This material exhibited slightly improved mechanical properties relative to the material of Example 5 and was capable of resisting approximately 5,000 gm-mm. of torsion, which is the maximum amount obtainable with a conventional 0.017"×0.025" stainless steel arch wire. In comparison, a conventional polycarbonate bracket will fail at approximatey 2,000 gm-mm torque. Optimum performance was obtained when the fibers were oriented 45° to 90° to the slot.

EXAMPLE 7

Example 5 was repeated using a polysulfone sold by LNP Corporation under the trade designation "GF-1008" in place of the polycarbonate, resulting in an orthodontic bracket that exhibited a flexure modulus of elasticity of $1.6 \times 10^6$ psi and a flexure strength of $27 \times 10^3$ psi. The material possessed excellent environmental stability, including resistance to stress-cracking, hydrolysis and discoloration and could be easily pigmented to provide the desired tooth coloration.

EXAMPLE 8

A number of different fiber reinforced composites were prepared using the same polymeric matrix but changing the type and amount of fiber used within the composition. The polymer employed was nylon 6—6 and the two fibers selected were carbon fibers and chopped glass fibers. The formulations were formed into wires and exhibited a modulus of elasticity within the range of 1 to $3.4 \times 10^6$ psi. Table I sets forth the fiber composition, the percent fiber utilized and the modulus and yield strengths for each of the materials.

TABLE I

| Formulation | Fiber | Vol. % Fiber | Flexure Modulus psi × 10⁶ | Flexure Yield Strength psi × 10³ |
|---|---|---|---|---|
| 8A | carbon | 10 | 1.0 | 20 |
| 8B | carbon | 20 | 2.4 | 28 |
| 8C | carbon | 30 | 2.9 | 35 |
| 8D | carbon | 40 | 3.4 | 40 |
| 8E | glass | 10 | 0.65 | 20 |
| 8F | glass | 30 | 1.3 | 38 |
| 8G | glass | 60 | 2.8 | 50 |

EXAMPLE 9

A fiber reinforced composite material was prepared having unusual anisotropic properties. This was formed from continuous strands or filaments of graphite preimpregnated with a partially polymerized epoxy. These preimpregnated strips were 12 inches wide and 0.0052 inches thick. The strips were layered and fully polymerized under moderate heat and pressure. However, the layers were oriented so that the relative fiber orientation varied between layers.

EXAMPLE 10

A series of simple experimental orthodontic brackets were produced from glass-filled polycarbonate composite material by injection into a heated aluminum mold having the cavity design such that the effects of different material properties and uncomplicated force systems could be more easily analyzed. The opening to the mold was intentionally placed in the base directly under the center of the slot, so as to obtain sufficient fiber orientation at 45° to the vertical dimension of the slot and in the occlusal-gingival plane. Fibers oriented at 90° to this position, but still in the occlusal-gingival plane, would be much less effective in improving the resistance of the bracket to torque from an orthodontic archwire.

Brackets were made with the clinically relevant wall thicknesses of 0.5, 1.0, 1.5 and 2.0 mm. To demonstrate the effect of fiber reinforcement, both infilled and 20 percent glass filled polycarbonate brackets were made in each wall thickness.

TABLE II

| Wall Thickness (mm) | Material | Max. Torque (gm-cm) | Max. Deflection (degree) |
|---|---|---|---|
| 0.5 | Unfilled | 160 | 30 |
|  | 20% glass | 180 | 27 |
| 1.0 | Unfilled | 195 | 35 |
|  | 20% glass | 265 | 32 |
| 1.5 | Unfilled | 350 | 45 |
|  | 20% glass | 400 | 25 |
| 2.0 | Unfilled | 290 | 35 |
|  | 20% glass | 550 | 30 |
| Stainless Steel |  | >600 | 8* |

*value when moment reaches 600 gm-cm.

Table II shows the maximum torque or moment that could be produced in each bracket as well as the deflection or amount of rotation of the wire in the bracket at the maximum moment. The improvement with fiber reinforcement can be readily noted. Of additional interest, the maximum torques approached that which can be produced by the commercial beta-titanium orthodontic wire, although still less than that which can be obtained with a similar size stainless steel wire.

EXAMPLE 11

A series of glass fiber-reinforced nylon orthodontic wires with nominal cross-sectional dimensions of 0.020"×0.025" and 0.025"×0.030" were injection-molded. The surfaces of the samples were smooth and the fibers were uniformly distributed and oriented predominantly parallel to the length of the wire, as shown in FIG. 3. Fiber loading was varied from 0% to 43%. Mechanical properties were measured in flexure with one inch span length specimens. As seen in Table III the modulus of elasticity increased with increasing fiber content but constant cross section.

TABLE III

| Sample | Size (in.) | Modulus (msi) Dry | Modulus (msi) Wet | Max. Bending Angle (degree) |
|---|---|---|---|---|
| Unfilled | 0.0206 × 0.0285 | 0.44 | 0.16 | >90 |
|  | 0.0323 × 0.0293 | 0.21 | 0.12 | >90 |
| 13% glass | 0.0286 × 0.0214 | 0.77 | 0.51 | >90 |
|  | 0.0328 × 0.0296 | 0.56 | 0.31 | >90 |
| 21% glass | 0.0216 × 0.0298 | 1.04 | 0.78 | 80 |
|  | 0.0332 × 0.0301 | 0.70 | 0.41 | 75 |
| 43% glass | 0.0217 × 0.0285 | 1.85 | 1.41 | 70 |
|  | 0.0331 × 0.0288 | 1.40 | 0.87 | 65 |

The springback of the fiber reinforced wires was comparable to or better than stainless steel at various deflections. Superior springback was more noticeable with shorter span lengths.

EXAMPLE 12

Six thermoplastic matrix formulations were injection-molded to form orthodontic-sized archwires. The samples were tested in flexure and the maximum torque and strain for each is reported in Table IV. The size of the wires was substantially the same as those set forth in Table III.

TABLE IV

| Material/ Crossection | Flexural Modulus (msi) | Max. Torque (gm-cm) | Max. strain (degree) |
|---|---|---|---|
| Polyacetal - 20% glass |  |  |  |
| small | 0.82 | 47.5 | 65–70 |
| large | 0.58 | 99.0 | 45–50 |
| Polyacetal - 40% glass |  |  |  |
| small | 1.51 | 50.2 | 30–35 |
| large | 1.11 | 90.0 | 25–30 |
| Polycarbonate - 20% glass |  |  |  |
| large | 0.46 | 95.1 | 45–50 |

TABLE IV-continued

| Material/Crossection | Flexural Modulus (msi) | Max. Torque (gm-cm) | Max. strain (degree) |
|---|---|---|---|
| Polyethylenterphthalate - 30% glass | | | |
| large | 0.97 | 102.7 | 30-40 |
| Polyethersulfone - 20% glass | | | |
| large | 0.67 | 118.8 | 45-50 |
| Polyphenylenesulfide - 40% glass | | | |
| small | 1.53 | 120.7 | 20-25 |
| large | 1.34 | 120.7 | 20-25 |

EXAMPLE 13

Commercially available continuous fiber sheets were laminated together to obtain a desired thickness, then cut to obtain desired final width and length dimensions for an orthodontic archwire. Table V lists the materials, the thickness of the starting sheets, and the results of flexure and tensile tests of the laminated samples. The bending moment of these wires increased almost linearly with activation. The lower range of flexure modulus values or stiffness for the continuous fiber wires as compared with stainless steel would impart clinically desirable lower and more continuous forces. The continuous fiber wires also had improved springback or recovery compared to stainless steel. After 80° deflection using a ¼ inch span, the aramid-filled composite recovered approximately 40°, while the stainless steel recovered only approximately 25°.

TABLE V

| Sample | Dimension (inch) | Flexure Test** ME (msi) | Tensile Test ME (msi) | Tensile Test YS (ksi) |
|---|---|---|---|---|
| Polyphenylene sulfide (PPS) | | | | |
| 60% Carbon | 0.007 | 8.7 | 4.0* | 77.0 |
| 60% aramid | 0.008 | 6 1 | | |
| PPS 2-ply | | | | |
| Carbon + Carbon | 0.014 | 9.6 | | |
| Carbon + aramid | 0.014 | 6.9 | | |
| PPS 3-ply Hybrid | | | | |
| aramid + Carbon + aramid | 0.021 | 5.7 | | |
| Unsaturated Polyester | | | | |
| aramid | 0.023 | 4.7 | 3.0* | 144.0 |
| Unsaturated Polyester | | | | |
| Carbon | 0.024 | 13.5 | 5.3* | 21.0 |
| Stainless | 0.018 | 22.9 | 9.9* | 284. |
| Steel | 0.016 | 23.7 | 12.8* | 250. |

ME = Modulus of Elasticity
YS = Yield Strength
*without strain gauge
**One inch span length As can be seen from the foregoing specific disclosure, the fiber reinforced composites of the present invention provide the clinical advantages of orthodontic wires that include greater springback and the ability to vary the stiffness of the wire without changing the size thereof. The cross section may remain constant or vary along its length. Additionally, the system can include control over the aesthetics of the devices, the formability thereof and the ability to provide unique cross sectional designs and incorporate unique design features within the various devices. Another advantage of the system of the present invention is that the devices do not interfere with nuclear magnetic resonance diagnostic testing procedures. Metal or metal alloys interfere with the images resulting from such testing whereas the fiber reinforced composite materials would not interfere with nuclear magnetic resonance analysis. These materials also can be readily bonded with adhesive, heat or ultrasonically thereby eliminating the soldering and electrical resistance welding necessary heretofore and can be formulated in unique wire, bracket and tube designs while modifying the frictional characteristics thereof as desired.

As will be apparent to persons skilled in the art, various modifications, adaptations and variations of the foregoing specific disclosure can be made without departing from the teachings of the present invention.

What is claimed is:

1. In an orthodontic appliance system for applying corrective forces to the teeth of a patient, the improvement wherein a force delivery component of the system is formed from a fiber reinforced composite material comprising a polymeric matrix and at least 5% by weight of reinforcing fibers embedded in the matrix, said composite material having a modulus of elasticity below $30 \times 10^6$ psi and a preselected ratio of Yield strength to modulus of elasticity within the range from a level comparable to that of 18-8 stainless steel up to at least 300 percent that of such stainless steel whereby more constant force levels can be applied with time and a continuous range of stiffness is achieved, said composite material having a higher maximum elastic deflection than said stainless steel and an ability to provide complex orthodontic configurations so as to enhance the ease and accuracy of force delivery.

2. The orthodontic appliance system of claim 1 wherein said fiber reinforced composite material has a modulus of elasticity in the range of $0.3-30 \times 10^6$ psi.

3. The orthodontic appliance system of claim 2 wherein said fiber is selected from the group consisting of continuous filaments and short fibers of inorganic, natural and synthetic organic materials.

4. The orthodontic appliance system of claim 2 wherein said matrix consists of thermoplastic or thermosetting material.

5. The orthodontic appliance system of claim 4 wherein said matrix material is selected from the group consisting of polyamides, polyesters, polyester glycols, polycarbonates, polyolefins, polyarylates, polyurethanes, polyacetals, polyarylsulfides, polysulfones and epoxies.

6. The orthodontic appliance system of claim 1 wherein said fiber reinforced composite material has a ratio of yield strength to modulus of elasticity in the range of $4 \times 10^{-3}$ to $40 \times 10^{-3}$ and a modulus of elasticity in the range of $0.5 \times 10^6$ to $25 \times 10^6$ psi.

7. The orthodontic appliance system of claim 1 wherein said fiber reinforced composite material contains about 5-80 percent short fiber and exhibits a modulus of elasticity up to about $5 \times 10^6$ psi.

8. The orthodontic appliance system of claim 1 wherein the fiber reinforced composite material contains continuous filaments and exhibits a modulus of elasticity in the range of about $1.5 \times 10^6$ psi to $25 \times 10^6$ psi.

9. The orthodontic appliance system of claim 1 wherein the fiber reinforced composite material has a predominant number of well dispersed fibers sufficiently in alignment to provide effective retention of the force delivery component during the application of said corrective forces.

10. In an orthodontic appliance system for applying corrective forces to the teeth of a patient, the improvement wherein the attachment component of the system is formed from a fiber reinforced composite material comprised essentially of a polymeric matrix and at least 10 percent by weight fibers desperced throughout the matrix and having a predominant orientation sufficient to effectively resist the maximum torque applied by the force delivery component.

11. The orthodontic appliance system of claim 10 wherein said fibers are selected from the group consisting of continuous filaments and short fibers of inorganic, natural and synthetic organic materials.

12. The orthodontic appliance system of claim 10 wherein said matrix consists of thermoplastic or thermosetting material.

13. The orthodontic appliance system of claim 10 wherein said matrix material is selected from the group consisting of polyamides, polyesters, polyester glycols, polycarbonates, polyolefins, polyarylates, polyurethanes, polyacetals, polyarylsulfides, polysulfones and epoxies.

14. The orthodontic appliance system of claim 10 wherein said fiber reinforced composite material contains up to 80 percent short fiber and exhibits a modulus of elasticity up to about $5 \times 10^6$ psi.

15. The orthodontic appliance system of claim 10 wherein the fiber reinforced composite material contains continuous filaments and exhibits a modulus of elasticity in the range of about $1.5 \times 10^6$ psi to $25 \times 10^6$ psi.

* * * * *